United States Patent
Lopez et al.

(10) Patent No.: US 8,084,421 B2
(45) Date of Patent: Dec. 27, 2011

(54) METHOD OF REDUCING BLOOD GLUCOSE LEVELS IN TYPE 2 DIABETES PATIENTS BY ADMINISTERING GRANULOCYTE-COLONY STIMULATING FACTOR

(76) Inventors: Carlos Lopez, Carmel, IN (US); James K. Petell, Grand Forks, ND (US); Fred Siegel, New York, NY (US)

( * ) Notice: Subject to any disclaimer, the term of this patent is extended or adjusted under 35 U.S.C. 154(b) by 0 days.

(21) Appl. No.: 12/401,173

(22) Filed: Mar. 10, 2009

(65) Prior Publication Data

US 2009/0170752 A1   Jul. 2, 2009

Related U.S. Application Data

(62) Division of application No. 11/462,546, filed on Aug. 4, 2006, now abandoned.

(60) Provisional application No. 60/705,707, filed on Aug. 4, 2005.

(51) Int. Cl.
*A61K 38/00* (2006.01)
*A61K 38/19* (2006.01)

(52) U.S. Cl. .................... 514/6.8; 424/198.1

(58) Field of Classification Search .............. None
See application file for complete search history.

(56) References Cited

U.S. PATENT DOCUMENTS 7,601,688 B2 * 10/2009 Still et al. .............. 514/3
7,662,366 B2 *  2/2010 Kawabe et al. .......... 424/85.1

* cited by examiner

*Primary Examiner* — Elly-Gerald Stoica
(74) *Attorney, Agent, or Firm* — James K. Petell

(57) ABSTRACT

A method for treating adult onset neurodegenerative diseases and diabetes by administering an effective dose of Granulocyte-Colony Stimulating Factors.

1 Claim, 3 Drawing Sheets

METHOD OF REDUCING BLOOD GLUCOSE LEVELS IN TYPE 2 DIABETES PATIENTS BY ADMINISTERING GRANULOCYTE-COLONY STIMULATING FACTOR

CROSS-REFERENCE TO RELATED APPLICATION

This application is a divisional of prior application Ser. No. 11/462,546, filed Aug. 4, 2006, which claims the benefit to U.S. Provisional Patent Application No. 60/705,707, filed Aug. 4, 2005, which are hereby incorporated herein by reference in their entirety.

FIELD OF INVENTION

A method for treating adult onset neurodegenerative diseases and diabetes by administering an effective dose of Granulocyte-Colony Stimulating Factors.

BACKGROUND OF THE INVENTION

Parkinson's disease is an example of a progressive neurodegenerative disease. It is usually diagnosed in adulthood, usually when the patient is about 55 years of age, and is characterized by tremors, rigidity, and bradykinesia. It is well understood that many of the abnormalities found in these patients are due to the loss of dopamine (DA) neurons in the substantia nigra and the depletion of striatal dopamine levels. More recently, there has been a re-evaluation of the signs and symptoms found in Parkinson's disease patients that has led to the conclusion that Parkinson's disease is a systemic disease with involvement of peripheral nervous tissue. For example, the loss of the sense of smell has been found to be an early sign of Parkinson's disease that is found in most patients. Often, the earliest sign of Parkinson's disease in patients is the loss of the sense of smell so that this symptom can be used as a diagnostic in patients with early disease. This symptom of disease is probably due to loss of neurons in the olfactory bulb of the brain. Also, orthostatic hypotension has been shown to be one of the more common signs of Parkinson's disease, probably due to a direct effect on the peripheral nervous system (PNS) of the host. Clinical manifestations of Parkinson's disease are not apparent until over 80% of the central or peripheral neurons have degenerated. Most new Parkinson's disease patients are started on dopamine agonists (DA) when first diagnosed, but usually progress to L-DOPA (L-dopamine), the precursor of dopamine in tissue. As a therapeutic, L-DOPA is used to relieve Parkinsonian motor signs, but has very little effect on PNS signs and symptoms of disease. In fact, its long-term use is usually associated with diminished efficacy and increasingly bothersome side effects. Other examples of chronic degenerative neurological disorders that might be treated in a similar manner include macular degeneration, urinary incontinence, Alzheimer's disease, Multiple Sclerosis and short term memory deficiency. These disorders have in common three characteristics; they are usually diagnosed late in life, there is evidence of familial, but not Mendelian genetic, inheritance of each disease, and patients will have had a period of time as adults before diagnosis of disease when the host appears to function normally without evidence of signs or symptoms of the chronic disease.

Over the past few years, tremendous strides have been made in understanding the crucial role that stem cells play in embryogenesis and organogenesis. Much of the accumulated data indicates that stem cells play an important role in the development and maturation of mammals. It is well known that each organ of the adult body contains progenitor stem cells that can respond to signals from other cells or injured tissue and migrate to the site of injury to help restore the tissue to normal health. In animal models, the "self-repair" system clearly responds to acute injury of tissues in the body and recruits stem cells from the bone marrow and other parts of the body to help with the repairs. Stem cells are also required to sustain those functional cell populations that turn over rapidly in the body such as skin and the various lymphocyte populations. The "self-repair" system is only now being demonstrated in human studies.

With the beginning of an understanding of the "self-repair" system and its probable role in response to tissue injury, researchers have proposed that delivering somatic progenitor stem cells directly to the site of damage might augment the hosts own "self-repair" system and more completely repair the damage to the host tissue. For example, neural stem cell lines have been successfully used to treat spinal cord injuries in mice and rats. However, this "self-repair" response appears to be determined by a complex interaction between cells and protein mediators produced by host and donor cells. Understanding the factors involved and their roles in this response and the differentiated state of the cells involved will be crucial to devising methods for controlling and utilizing this system for providing new therapies for chronic diseases. Studies are ongoing in many laboratories to further define the factors and cells involved. Most recently, continuous infusion of Glial-Derived Neurotrophic Factor (GDNF), a stem cell growth factor, directly into the brain has been claimed to have benefit for patients with Parkinson's disease. When analyzed statistically, the clinical study involving treatment with GDNF by Amgen was found to be unsuccessful in generating a positive impact on either stabilizing or reversing the symptoms of Parkinson's Disease.

Over the past several years, significant interest has developed in using mobilized peripheral blood progenitor cells for allogeneic hematopoietic reconstitution. Treatment of stem cell donors with a five-day course of Granulocyte-Colony Stimulating Factor or its pegalated derivative causes the release of stem cells from the bone marrow into the circulating blood and greatly increases the number of hematopoietic and other stem cells that could be harvested from the donor. This procedure requires Granulocyte-Colony Stimulating Factor be administered to otherwise normal donors in order to release stem cells into the peripheral blood where they can be collected by leukophoresis and prepared for transplantation. Many studies have reported the use of Granulocyte-Colony Stimulating Factor in normal volunteers and normal donors, usually at a dose of 5 to 10 micrograms per kg per day for 4 to 8 days. The most common toxicities were bone pain, headaches, and fever. While the toxicities were frequent, the severity was generally mild and very few normal donors had to discontinue Granulocyte-Colony Stimulating Factor because of the side effects. Persons treated with Granulocyte-Colony Stimulating Factor were found to have a surge in peripheral blood stem cells 4 to 7 days after initial treatment. The use of Granulocyte-Colony Stimulating Factor for mobilizing peripheral blood stem cells is widespread and appears to be safe and to be capable of generating the stem cells needed for allogenic or autologous transplantation.

Although the above studies suggest Granulocyte-Colony Stimulating Factor is capable of mobilizing peripheral hematopoietic stem cells, it is not known if Granulocyte-Colony Stimulating Factor could induce the recruitment of either local or migration of peripheral stem cells to injured neural tissue, differentiate and restore neural function required for the slowly developing lesions found in most chronic diseases. Further, to our knowledge a "self-repair" system has not been described in human studies.

Diabetes is a major public health problem in the United States affecting 16 million people and accounts for one sixth of all health related expenditures. There are two types; Type 1 and Type 2 (formerly referred to as noninsulin-dependent diabetes). Type 1 is characterized by beta cell loss and absolute insulin deficiency. Of the patients with diabetes today, approximately 90 to 95% of the inflicted are Type 2 diabetics. It is generally characterized by elevated fasting blood glucose and lack of sensitivity to insulin and impaired insulin secretion. The prevalence of Type 2 diabetes is about 7 percent for persons between 45 to 64 years of age. The microvascular and macrovascular complications of Type 2 diabetes causes significant morbidity and mortality in affected individuals. Diabetic retinopathy, neuropathy, and nephropathy are major causes of functional limitations and disability in this patient population. In the event that diet and exercise are not sufficient to control blood glucose, diabetics may be treated with one, and typically two, of several oral drugs able to lower blood glucose levels which include sulfonylureas, metformin, alpha-glucosidase, troglitazone, and repaglinide. These agents act on one of four mechanisms that alter renal function, liver metabolism, insulin secretion or breakdown of complex carbohydrates. If these drugs are insufficient, insulin treatment may be prescribed alone or together with these oral agents.

Improved glycemic control reduces the risk of microvascular complications in Type 2 diabetes. Despite this evidence, patients with Type 2 diabetes frequently do not maintain adequate glycemic control. However, the health outcomes of patients with Type 2 diabetes who are treated with insulin to control glycemia do much better than those that do not. Patients are encouraged to use intensive insulin treatment protocols to better control blood sugar but analysis of their outcomes indicate that it did not affect the quality of life of patients in the intensive insulin treatment nor did it have a significant protective effect against cardiovascular diseases. There is evidence that tight glycemic control will decrease the incidence of microvascular complications so patients should be encouraged to use insulin and oral hypoglycemic agents. However, it is difficult to make a convincing argument to patients that do not currently have severe symptoms of disease associated with their elevated blood sugar levels. There are no other forms of medical treatment to lower blood glucose to an acceptable range. The ideal drug for these patients is one where a single drug can be taken periodically that is able to control blood glucose levels over the course of a week or longer with reduced side affects.

It is unknown whether the chronic progressive neurodegenerative and non-neurodegenerative disorders could be treated effectively by mobilizing the "self-repair" mechanism of the host or even if that "self-repair" mechanism could be detected in patients with these disorders. Furthermore, Parkinson's disease in humans is a systemic disease with symptoms that indicate the PNS is an important target tissue of this disease. Surprising, this invention directly demonstrated for the first time in humans the potential action of Granulocyte-Colony Stimulating Factors, known to mobilize stem cells into the peripheral blood as well as to cause them to differentiate as a therapy to reverse symptoms of an adult onset neurodegenerative disorder such as Parkinson's disease. In addition, it was more surprising that Type 2 diabetes was found to be effectively controlled by periodically administering of Granulocyte-Colony Stimulating Factors offering a new approach and a revolutionary treatment for this disease. In both cases of adult onset disease the administered patient was provided a long term reversal of disease symptoms allowing a more normal lifestyle, a better efficacy for control, an extended period of control without a daily drug requirement, and the potential for reduced side effects for treatment.

SUMMARY OF THE INVENTION

The present invention is directed to provide a method of treating symptoms associated with a neurodegenerative disease in a human by administering an effective dose of Granulocyte-Colony Stimulating Factor or its derivatives, Granulocyte-Macrophage Colony Stimulating Factor or its derivatives, or combinations thereof. More preferably, the invention is directed to provide a method for the reversal of symptoms associated with Parkinson's Disease in a human through periodically administering of Granulocyte-Colony Stimulating Factor or its derivatives, Granulocyte-Macrophage Colony Stimulating Factor or its derivatives, or combinations thereof.

In another aspect, the invention herein is directed to provide a method of treating symptoms associated with diabetes in humans by administering an effective dose of Granulocyte-Colony Stimulating Factor or its derivatives, Granulocyte-Macrophage Colony Stimulating Factor or its derivatives, or combinations thereof. More preferably, the invention is directed to provide a method for the extended reduction of blood glucose levels associated with Type 2 diabetes in a human through administering of Granulocyte-Colony Stimulating Factor or its derivatives, Granulocyte-Macrophage Colony Stimulating Factor or its derivatives, or combinations thereof.

In the first aspect of the invention, one or more symptoms of an adult onset neurodegenerative disease are treated by administering to a human an effective dose of Granulocyte-Colony Stimulating Factor or its derivatives, Granulocyte-Macrophage Colony Stimulating Factor or its derivatives, or combinations thereof. Adult onset neurodegenerative diseases include but are not limited to Parkinson's Disease, macular degeneration, urinary incontinence, age related short term memory loss, and multiple sclerosis. More preferably, one or more symptoms of adult onset Parkinson's disease are reversed by administering an effective dose of Granulocyte-Colony Stimulating Factor or its derivatives, Granulocyte-Macrophage Colony Stimulating Factor or its derivatives, or combinations thereof.

In the second aspect of the invention, an effective dose of Granulocyte-Colony Stimulating Factor or its derivatives, Granulocyte-Macrophage Colony Stimulating Factor or its derivatives, or combinations thereof is administered to a human with an adult onset neurodegenerative disease by subcutaneous injection, transdermal patch, intravenously, orally or other means. A typical period for administering Granulocyte-Colony Stimulating Factors is from about 1 to 8 days, preferably ranging 3 to 6 days.

In a third aspect of the invention an effective dose of Granulocyte-Colony Stimulating Factor or its derivatives, Granulocyte-Macrophage Colony Stimulating Factor or its derivatives, or combinations thereof are administered daily to a human for treatment of an adult onset neurodegenerative disease ranging from 0.1 micrograms to 20000 micrograms per kg body weight per day, preferably between 1 to 20 micrograms per kg body weight per day.

In a fourth aspect of the invention an effective dose of Granulocyte-Colony Stimulating Factor or its derivatives, Granulocyte-Macrophage Colony Stimulating Factor or its derivatives, or combinations thereof is administered to a human for treatment of an adult onset neurodegenerative disease for about 1 to 8 days and repeated about every 2 to 18 weeks, and more preferably every 4 to 10 weeks.

In a fifth aspect of the invention an effective dose of Granulocyte-Colony Stimulating Factor or its derivatives, Granulocyte-Macrophage Colony Stimulating Factor or its derivatives, or combinations thereof is administered into a human for the reversal of one or more symptoms associated with Parkinson's Disease. Symptoms of Parkinson's Disease may be either central nervous system or peripheral nervous system derived and, include but are not limited to, orthostatic hypotension, resting tremor, rigidity, postural instability, micrographia, urinary and gastrointestinal incontinence and lack of sense of smell.

In a sixth aspect of the invention an effective dose of Granulocyte-Colony Stimulating Factor or its derivatives, Granulocyte-Macrophage Colony Stimulating Factor or its derivatives, or combinations thereof is administered into a human with an adult onset neurodegenerative disease in combination with stem cells a selected from a group consisting of harvested umbilical cord stem cells, progenitor stem cells or stem cell lines. In a related aspect, harvested stem cells, progenitor stem cells or stem cell lines are pre-treated with Granulocyte-Colony Stimulating Factor or its derivatives, Granulocyte-Macrophage Colony Stimulating Factor or its derivatives, or combinations thereof before injection.

In a seventh aspect of the invention, the level of blood glucose in an adult onset Type 2 diabetic is reduced by treatment with an effective dose of Granulocyte-Colony Stimulating Factor or its derivatives, Granulocyte-Macrophage Colony Stimulating Factor or its derivatives, or combinations thereof. Preferably the blood glucose levels after treatment remain reduced by 2 days longer, more preferably 1 week or longer and most preferably 4 weeks or longer.

In the eighth aspect of the invention, an effective dose of Granulocyte-Colony Stimulating Factor or its derivatives, Granulocyte-Macrophage Colony Stimulating Factor or its derivatives, or combinations thereof is administered into a human for treatment of diabetes, and preferably Type 2 diabetes, by subcutaneous injection, transdermal patch, intravenously, orally or other means. A typical period for administering is from about 1 to 8 days, more preferably ranging 3 to 6 days.

In the ninth aspect of the invention an effective dose of Granulocyte-Colony Stimulating Factor or its derivatives, Granulocyte-Macrophage Colony Stimulating Factor or its derivatives, or combinations thereof administered into a human for treatment of diabetes ranging from 0.1 micrograms to 20000 micrograms per kg body weight per day, preferably between 1 micrograms to 20 micrograms per kg body weight per day.

In the tenth aspect of the invention an effective dose of Granulocyte-Colony Stimulating Factor or its derivatives, Granulocyte-Macrophage Colony Stimulating Factor or its derivatives, or combinations thereof is administered for treatment of Type 2 diabetes for about 1 to 8 days and the treatment is repeated about every 2 to 18 weeks, and preferably every 4 to 10 weeks. Preferably, Granulocyte-Colony Stimulating Factors is administered at least one weeks before the blood glucose levels rise to levels prior treatment.

In an eleventh aspect of the invention, Granulocyte-Colony Stimulating Factor or its derivatives, Granulocyte-Macrophage Colony Stimulating Factor or its derivatives, or combinations thereof is effective in improving other brain associated neural diseases that include but are not limited age related memory impairment, Schizophrenia, and Alzheimer's.

"Granulocyte-Colony Stimulating Factors" means Granulocyte-Colony Stimulating Factor or its derivatives, Granulocyte-Macrophage Colony Stimulating Factor or its derivatives, or other biologically or chemically derived compounds or factors that are functional equivalent.

"Maintaining" means slowing, interrupting, arresting or stopping the progression of the disease.

"Reversing" means the improvement of one or more symptoms from the diseased state rather than maintaining the current state of disease.

"Treat" means maintaining the state of the disease or the reversal of a disease symptom.

DETAILED DESCRIPTION OF INVENTION

Figure 1:
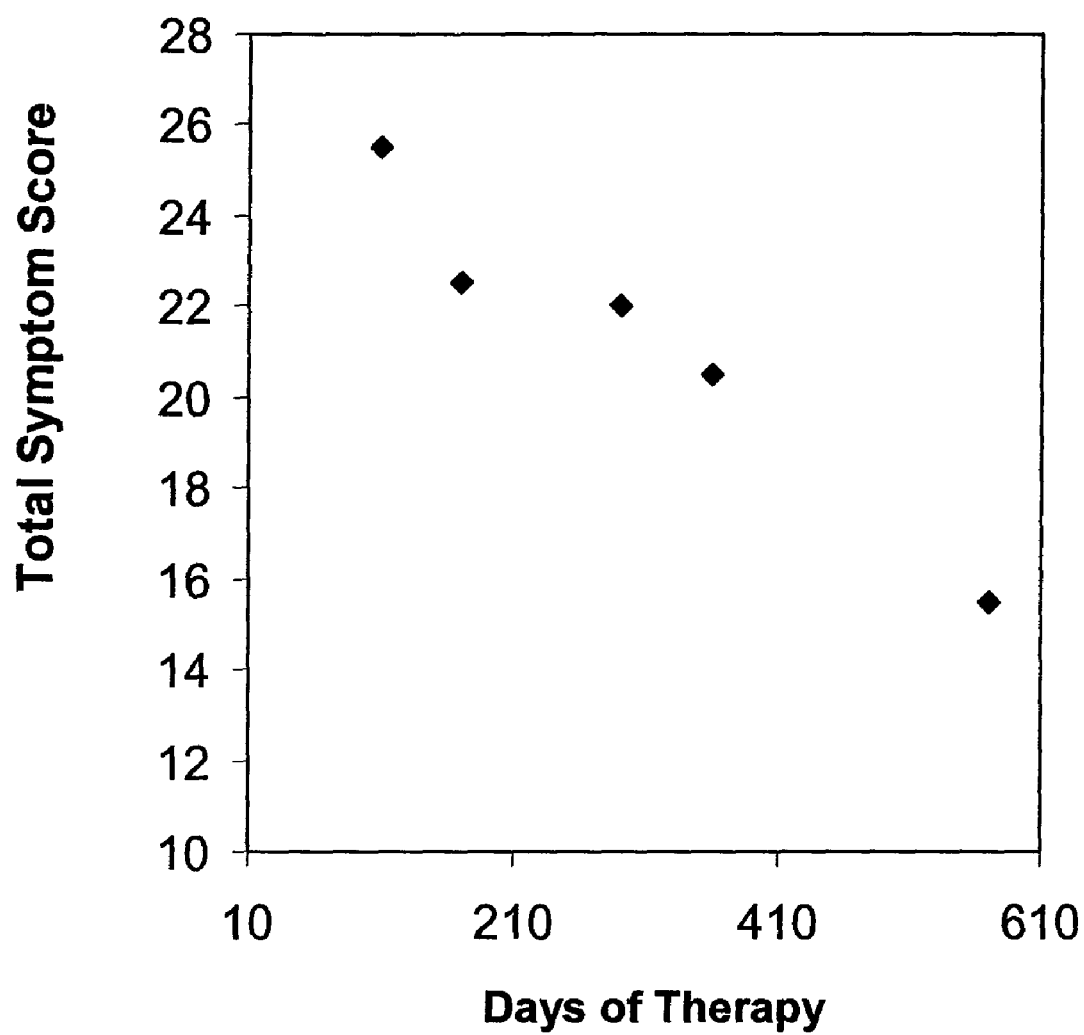
FIG. 1 demonstrates the long term reversal of Parkinson's Disease symptoms using the United Parkinson's Disease Scale to evaluate the condition of the patient administered with Granulocyte-Colony Stimulating Factor over two and one-half years.
Figure 2:
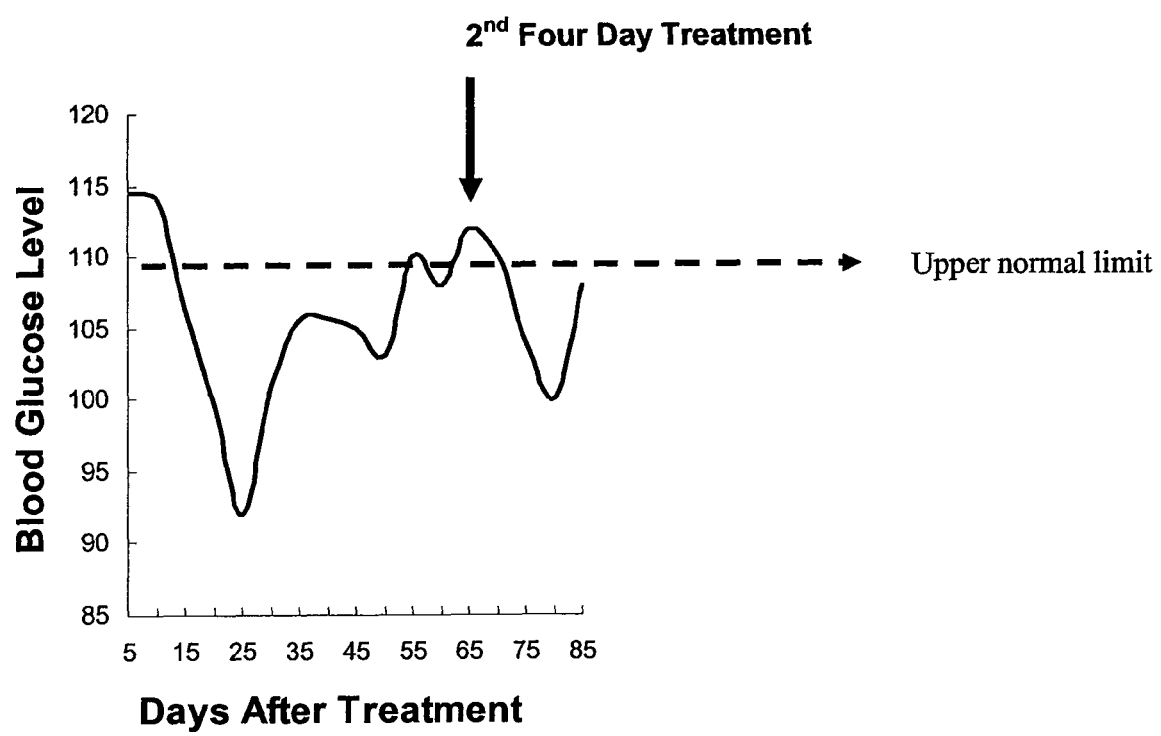
FIG. 2 demonstrates the reduction of blood glucose levels below the preferred normal limit after Granulocyte-Colony Stimulating Factor was administered to Type 2 diabetic patient.

The present invention described herein was aimed at performing treatments using Granulocyte-Colony Stimulating Factors administered to patients with neurodegenerative diseases, more preferably Parkinson's disease, to determine whether Granulocyte-Colony Stimulating Factors were able to maintain the state of the diseases, and preferably reverse the symptoms, either partially or completely. Unexpectedly, it was found that the treatment of the neurodegenerative disease, Parkinson's Disease, with Granulocyte-Colony Stimulating Factors reversed symptoms of both the central nervous system (CNS) and peripheral nervous system (PNS). In addition, it was found that Granulocyte-Colony Stimulating Factors delivered in an effective dose was able to reduce blood sugar levels of patients with adult onset Type 2 diabetes for a significant period of time.

The nucleic acid sequence and encoded amino acid sequence of Granulocyte-Colony Stimulating Factor (GCSF), also referred to as human pluripotent granulocyte colony-stimulating factor, as well as chemically synthesized polypeptides sharing its biochemical and immunological properties has been previously disclosed (U.S. Pat. Nos. 6,379,661; 6,004,548; 6,830,705; 5,676,941; 6,027,720; 5,994,518; 5,795,968; 5,214,132; 5,218,092; 6,261,550; 4,810,643; 4,810,321). Other examples of Granulocyte-Colony Stimulating Factor include analogs which retained their three-dimensional structures and hybrid molecules maintaining their biological and structural integrity were described by Osslund (U.S. Pat. No. 6,261,550). Examples of functional GCSF variants include any proteins, peptides or fragments thereof that are at least 70%, preferably 80% and most preferably at least 90% identity to full-length human GCSF amino acid sequence or its nucleotide sequence. Modifications of GSCF to improve functionality or resident serum clearance include but are not limited to polyethyleneglycol and polyethyleneglycol derivatives thereof, glycosylated forms (Lenogastrim™) (WO 00/44785), norleucine analogs (U.S. Pat. No. 5,599,690), addition of amino acids at either terminus to improve folding, stability or targeting, and fusion proteins, such as GCSF and albumin fusion protein (Albugranin™) (U.S. Pat. No. 6,261,250). An increase in biological or functional activity over the native peptide may reduce the amount of dose and/or the time period required for treatment. Any chemical or biological entity that functions similar to GCSF can also be employed. GCSF, or the drug name Filgrastim, is currently being sold as Neupogen® and its polyethylene glycol modified or pegulated form, with the drug name Pegfilgrastim, sold as Neulasta™.

Examples of closely related functional forms include Granulocyte-Macrophage Colony Stimulating Factor (GMCSF) whose coding DNA sequence and protein including amino acid sequence are known as well as various methods employed to produce recombinant proteins (U.S. Pat. No. 5,641,663). Examples of functional GMCSF variants include any proteins, peptides or fragments thereof that are at least 70%, preferably 80% and most preferably at least 90% identity to full-length human GMCSF amino acid sequence or its nucleotide sequence. Modifications of GSCF to improve functionality or resident serum clearance include but are not limited to polyethyleneglycol and polyethyleneglycol derivatives thereof, glycosylated forms, norleucine analogs, addition of amino acids at either terminus to improve folding, stability or targeting, and fusion proteins, such as GCSF and albumin fusion protein (Albugranin™). An increase in biological or functional activity over the native peptide may reduce the amount of dose and/or the time period required for treatment. Any chemical or biological entity that functions similar to GMCSF can also be employed. Examples of GMCSF, or the drug name Sargramostim, which are currently being sold, include Leukine® or Leucomax® and Leucotropin®.

Other compounds known as AMD3100 or derivatives thereof (U.S. Pub. No. 2002/0058653, 2003/0130250, U.S. Pat. No. 6,670,354) effective in enhancing or elevating the populations of progenitor and/or stem cells may be used in conjunction with GSCF or GMCSF derivatives or combinations thereof. Treatments with compounds may be administered at the same time or prior to administration of GSCF or GMCSF.

In one embodiment oral dosages, and methods thereof, of Granulocyte-Colony Stimulating Factor have been described by Nomura and Kazutoshi (U.S. Pat. No. 5,597,562) that allow for dosage reductions, facilitate dose control, and increase the practical usefulness of the bioactive proteins. In addition, Brimelow and Nanette (U.S. Pat. No. 6,497,689) have described preferred pH ranges comprising sulfate ions for stabilizations.

Granulocyte-Colony Stimulating Factors has been suggested to act as a neuroprotective agent in vitro and may be used for the potential treatment of diseases that result from oxidative stress or apoptosis such as in cerebral ischemia and traumatic brain injury (U.S. Pub. No. 2004/0141946; 2006/0153799). The work was focused on an in vitro model using STAT proteins and GCSF receptor or rat model for cerebral ischemia. It was suggested that GCSF may be used to "treat" broadly ischemic or hypoxic related diseases as well as neurological, psychiatric and neurodegenerative diseases as neuroprotective agent acting to slow, interrupt, arrest or stop the progression of the disease. However the work fails to provide insights on how treatment would work in humans as no human study was performed.

Type 2 diabetes is an example of a non-neurological disorder that appears to be due to the lack of insulin sensitivity of the target cells or insufficient levels of insulin in response to blood glucose. Although it is unknown what causes Type 2 diabetes, it is clear that the disease is usually first diagnosed as an adult and is usually progressive (in terms of the need for therapy to control blood sugar). Type 2 diabetics will have had a relatively long period of time with normal blood sugar before the fasting blood sugar levels begin to rise and the disease can be diagnosed. Other non-neurological disorders include osteoarthritis and benign prostate hypertrophy.

In view of ongoing research work on stem cells, the use of Granulocyte-Colony Stimulating Factors are likely to enhance or be required in the treatment of neurodegenerative diseases by stem cell therapy. For example, a method for the differentiation of stem cells in culture using Granulocyte-Colony Stimulating Factor and other factors, including lipopolysaccharides, to obtain immune system suppressor cells and immune systems stimulator cells was described by Ogle et al (U.S. Pat. No. 6,165,785). Using a similar approach, a method is useful in differentiating stem cells that are destined to become replacements for damaged cells in neurodegenerative disease and diabetes. Upon pretreatment of stem cells with Granulocyte-Colony Stimulating Factors, injected stimulated stem cells into patients with adult onset Type 2 diabetes and adult onset neurodegenerative diseases, such as Parkinson's Disease, are able to initiate repair or to enhance the effect over Granulocyte-Colony Stimulating Factors alone. The patients provided these stem are also administered Granulocyte-Colony Stimulating Factors for further benefit. Alternatively, patients with the adult onset diseases are injected with stem cells that are not pretreated with Granulocyte-Colony Stimulating Factors but subsequent treatment and provided with an effective dose of Granulocyte-Colony Stimulating Factors to enhance response.

Example 1

Reversal of Symptoms with Parkinson's Disease with Granulocyte-Colony Stimulating Factor The patient was a 61 year-old male with a six year history of Parkinson's Disease. When first diagnosed two years prior, the patient was started on 100 milligrams Amantidine twice daily and 5 milligrams Selegiline twice daily and on increasing doses of Permax, 25 micrograms to 250 micrograms three times daily.

A history taken immediately before starting the dosing of Granulocyte-Colony Stimulating Factor (GCSF) was typical of adult onset Parkinson's disease. The patient had blood work performed 7 days before treatment which included CBC, ESR, urine analysis and chemistry screen. In summary, the male patient, approximately 67 kg body weight diagnosed with Parkinson's Disease had history of modest hyperlipidemia which was controlled on medications. Physical exam was normal except for some cogwheeling especially on the right. Granulocyte-Colony Stimulating Factor was started at a daily dose of 330 micrograms (1.1 ml) through injection for 5 consecutive days. Patient experienced slight bone pain on second and third days of therapy. About 3 weeks after Granulocyte-Colony Stimulating Factor therapy was started, patient realized that he could smell, something that he had not been able to do for more than 5 years. This observation is consistent with improvement in olfactory nerve function. About a week later, the patient found that the orthostatic hypotension that had given him trouble for the last 2-3 years and had required him to wear support stockings, had disappeared. In addition, the patient was able to stand up quickly from a sitting position or walk up stairs without becoming severely light-headed. The patient's handwriting, previously totally unreadable, was greatly improved and was legible to others. It was observed that the patient had an improved facial affect. After about two months, a plateau was reached.

Surprisingly, it was found that Granulocyte-Colony Stimulating Factor treatment of a patient with Parkinson's disease was followed four weeks later by quantifiable evidence of efficacy utilizing symptoms that indicated an effect on both the Central Nervous System and Peripheral Nervous System (PNS). The patient improved in several CNS symptoms which included resting tremor, rigidity, postural instability, and micrographia. Four well accepted PNS symptoms of Parkinson's disease, the loss of sense of smell, orthostatic hypotension and urinary and gastrointestinal incontinence disappeared during the third and fourth weeks following the start of therapy. The disappearance of orthostatic hypotension was not complete but was greatly reduced. Unexpectedly, GCSF caused reversal of one or more symptoms of Parkinson's Disease upon treatment with the first dose. The reversed symptoms included orthostatic hypotension, resting tremor, rigidity, postural instability, handwriting and urinary and gastrointestinal incontinence.

Example 2

Long Term Treatment of Parkinson's Disease using Granulocyte-Colony Stimulating Factor The long term treatment of Parkinson's Disease by GCSF was followed using a standardized system approved by neurologists, the Unified Parkinson's Disease Scale (UPDS), to more completely access the efficacy of treatment. UPDS utilizes over 40 distinct clinical evaluations that are predominantly based mainly on CNS symptoms. Analysis was performed approximately 2 to 4 weeks after injection of the first dose. To more fully understand the effect of the GCSF, the data was analyzed to determine whether a correlation existed between dose of GCSF and reversal of symptom score. The patient received injection of the same dose of GCSF every six to eight weeks and was periodically evaluated by UPDS criteria. In FIG. 1, the score of UPDS was plotted over the course of two and one-half years. The correlation coefficient was −0.93 suggesting the reversal was progressive upon GCSF treatment and was statically significant (P=0.001). The final score obtained by the patient approached the score of a normal individual.

Because UPDS evaluates mostly CNS symptoms of Parkinson's Disease, four indicators of PNS symptoms were also evaluated included urinary and gastrointestinal incontinence, orthostatic hypotension and loss of smell. The induction of orthostatic hypotension was evaluated by taking blood pressure before and after going from a lying down position to sitting and then standing position and each time taking blood pressure with an automatic apparatus. A drop of 50 mm was associated with developing lightheadedness and orthostatic hypotension. All four indicators were reversed relative to the state prior to GCSF treatment. In fact, the patient was able to exercise without fainting or having to rest (orthostatic hypotension), enjoyed foods and drinks (smell), resolved urinary and gastrointestinal incontinence, and gained sense of smell resulting in a higher quality of life.

Example 3

Reduction of Blood Glucose Levels in Type 2 Diabetics Administered with Granulocyte-Colony Stimulating Factor Other benefits were observed upon treatment with Granulocyte-Colony Stimulating Factor in the same patient as described in Example 1. The patient exhibited a two year history of slightly elevated blood glucose determinations (average fasting blood sugar ranging up to 115 mg/Dl). Patient had a slightly elevated hemoglobin A1C (6.5 versus normal of <6.0. He was diagnosed as Type 2 Diabetes and was recommended to a "Diabetes" clinic for classes on diet and exercise for dealing with this disease. Although dieting and exercise provided some reducing it was not solely sufficient in controlling blood glucose levels below the 110 mg/dl.

After treatment with Granulocyte-Colony Stimulating Factor it was observed that the blood sugar averaged 104 mg/Dl for 15 specimens before treatment and decreased to 92 mg/Dl during the period starting three weeks after the start of drug (and at the same time that Parkinson's symptoms disappeared. The difference was highly significant (P=0.001).

Example 4

Figure 3:
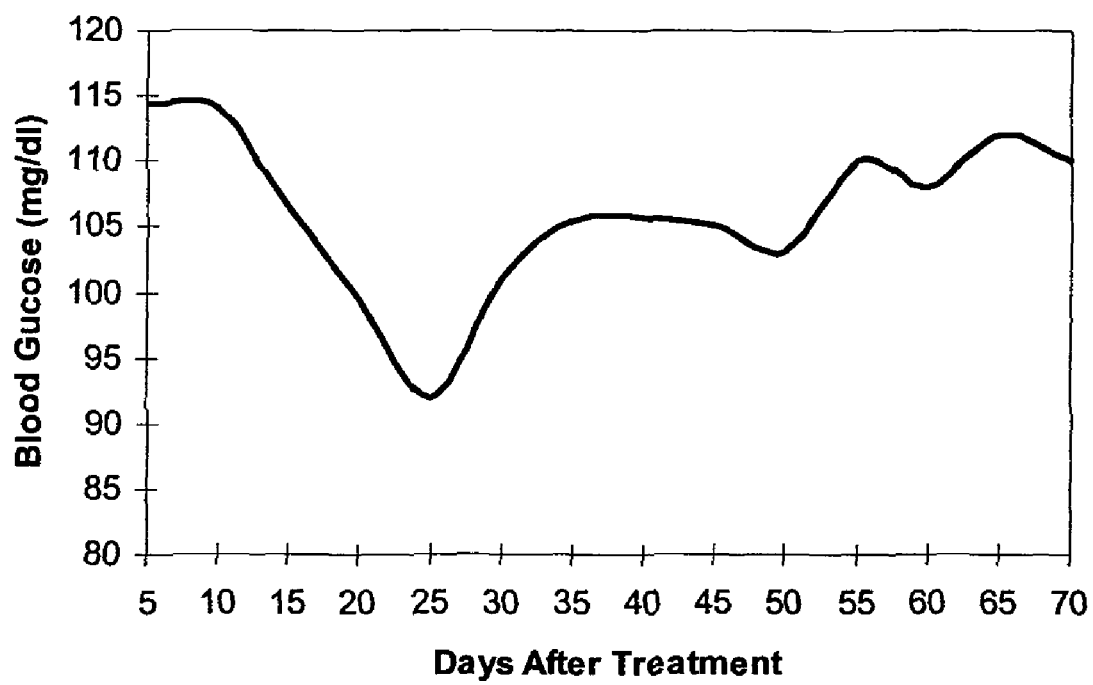
FIG. 3 shows the average time course for blood glucose levels of six treatments with GCSF.

Long Term Controlled Reduction of Blood Glucose Levels in Type 2 Diabetics Administered with Granulocyte-Colony Stimulating Factor To examine the long term effect of Granulocyte-Colony Stimulating Factor on a patient with adult onset Type 2 diabetes, the patient in Example 2 was monitored for approximately two and one-half years for fasting blood glucose almost every morning. Starting with the first day of therapy with GCSF, every 5 day period was averaged and the mean used to compare blood glucose levels. FIG. 3 shows the analyzed data from blood sugar determinations around six courses of GCSF. Each time after the GCSF is administered the blood sugar dropped well within the normal range after about twenty to thirty days after the start of therapy. In one case drug was not administered until late in the period of follow-up and then the nadir was reached about twenty-five days after the start of that course. All curves reached a nadir ranging between 20 and 30 days after the start of therapy. Most blood glucose determinations remained below 110 mg/Dl for about 2 months after treatment. It was unexpected that a drug, and more surprising GCSF, is able to reduce blood glucose for extended periods beyond one day, even more surprising one week and most surprising one month. The patient was also able to ingest limited amounts of Dove® bars without any problems. GCSF provides a consistent and more desirable approach to regulate blood glucose levels in Type 2 diabetics with less potential side effects of multiple mechanisms employed to control Type 2 diabetes beyond other drugs.

Other Embodiments

The description of the specific embodiments of the invention is presented for the purposes of illustration. It is not intended to be exhaustive nor to limit the scope of the invention to the specific forms described herein. Although the invention has been described with reference to several embodiments, it will be understood by one of ordinary skill in the art that various modifications can be made without departing from the spirit and the scope of the invention, as set forth in the claims. All patents, patent applications, and publications referenced herein are hereby incorporated by reference.

Other embodiments are within the claims.

The invention claimed is:

1. A method of reducing blood glucose level for at least 4 weeks in Type 2 diabetes in a human, comprising administering two or more courses of an effective dose of a Granulocyte-Colony Stimulating Factor, further comprising monitoring blood glucose level after the administration of an effective dose of Granulocyte-Colony Stimulating Factor and repeating a course of a Granulocyte-Colony Stimulating Factor every 2 to 18 weeks when blood glucose level is elevated over normal blood glucose level.

* * * * *